United States Patent
Lowe et al.

(10) Patent No.: US 9,844,518 B2
(45) Date of Patent: Dec. 19, 2017

(54) METHODS OF GROWING CANNABACEAE PLANTS USING ARTIFICIAL LIGHTING

(71) Applicant: MJAR Holdings, LLC, Miami, FL (US)

(72) Inventors: James Lowe, Denver, CO (US); Benjamin Franz, Denver, CO (US); Matthew Curran, Denver, CO (US)

(73) Assignee: MJAR Holdings, LLC, Miami, FL (US)

( * ) Notice: Subject to any disclaimer, the term of this patent is extended or adjusted under 35 U.S.C. 154(b) by 6 days.

(21) Appl. No.: 14/871,829

(22) Filed: Sep. 30, 2015

(65) Prior Publication Data

US 2016/0184237 A1 Jun. 30, 2016

Related U.S. Application Data

(60) Provisional application No. 62/058,045, filed on Sep. 30, 2014.

(51) Int. Cl.
| | | |
|---|---|---|
| A01G 7/04 | (2006.01) | |
| A61K 31/05 | (2006.01) | |
| A01G 1/00 | (2006.01) | |
| A01G 25/00 | (2006.01) | |
| A61K 36/185 | (2006.01) | |

(52) U.S. Cl.
CPC ............ *A61K 31/05* (2013.01); *A01G 1/001* (2013.01); *A01G 7/04* (2013.01); *A01G 7/045* (2013.01); *A01G 25/00* (2013.01); *A61K 36/185* (2013.01)

(58) Field of Classification Search
CPC . A01G 1/00; A01G 1/001; A01G 7/00; A01G 7/04; A01G 7/045; A01G 7/06; A01G 9/00; A01G 9/14; A01G 9/20; A01G 9/24; A01G 9/246; A01G 9/247; A01G 9/26; A01G 17/00; A01G 17/005; A01G 25/16; A01G 25/162; A01G 25/167; A01G 31/02; A01G 25/165
See application file for complete search history.

(56) References Cited

U.S. PATENT DOCUMENTS

| | | |
|---|---|---|
| 4,908,985 A | 3/1990 | Dowell |
| 5,130,325 A | 7/1992 | Smith |
| 6,178,691 B1 | 1/2001 | Caron et al. |
| 6,503,532 B1 | 1/2003 | Murty et al. |
| 6,509,005 B1 | 1/2003 | Peart et al. |

(Continued)

FOREIGN PATENT DOCUMENTS

| | | |
|---|---|---|
| CN | 103120100 | 5/2013 |
| EP | 1 361 864 | 11/2003 |

(Continued)

OTHER PUBLICATIONS

"Weed farmer" http://www.weedsthatplease.com/germinating.htm.*

(Continued)

*Primary Examiner* — Thanh Pham
(74) *Attorney, Agent, or Firm* — Cooley LLP; Nathan W. Poulsen; Marcelo C. Pomeranz

(57) ABSTRACT

This invention is directed to a method of growing a plant from the Cannabaceae family, the cultivar or composition produced therefrom, wherein the plant is exposed to artificial lighting of different intensities based on spacing, growth phase, and flowering yield.

7 Claims, 1 Drawing Sheet

(56) References Cited

U.S. PATENT DOCUMENTS

| | | | |
|---|---|---|---|
| 6,630,507 | B1 | 10/2003 | Hampson et al. |
| 6,730,330 | B2 | 5/2004 | Whittle et al. |
| 6,747,058 | B1 | 6/2004 | Dedhiya et al. |
| 7,025,992 | B2 | 4/2006 | Whittle et al. |
| 7,105,685 | B2 | 9/2006 | Travis |
| 7,109,245 | B2 | 9/2006 | Kunos et al. |
| 7,647,724 | B2 | 1/2010 | Caron et al. |
| 7,968,594 | B2 | 6/2011 | Guy et al. |
| 8,629,177 | B2 | 1/2014 | Castor et al. |
| 8,771,760 | B2 | 7/2014 | Guy et al. |
| 8,790,719 | B2 | 7/2014 | Parolaro et al. |
| 8,847,514 | B1 * | 9/2014 | Reynoso ............. A01G 7/045 315/307 |
| 9,095,554 | B2 | 8/2015 | Lewis et al. |
| 2004/0144025 | A1 * | 7/2004 | Johnson Rutzke ...... A01G 7/06 47/57.7 |
| 2008/0298052 | A1 * | 12/2008 | Hurst ................. A01G 7/045 362/231 |
| 2010/0286098 | A1 | 11/2010 | Robson et al. |
| 2011/0098348 | A1 * | 4/2011 | De Meijer ............. A01H 5/12 514/456 |
| 2011/0257256 | A1 | 10/2011 | Fuchs et al. |
| 2011/0302839 | A1 | 12/2011 | Senders et al. |
| 2012/0287617 | A1 * | 11/2012 | Mekhtarian ........... A01G 7/045 362/228 |
| 2012/0311744 | A1 * | 12/2012 | Sirkowski ............ G01N 21/64 800/298 |
| 2013/0059018 | A1 | 3/2013 | Parolaro et al. |
| 2014/0259905 | A1 | 9/2014 | Ovadya et al. |
| 2015/0208590 | A1 * | 7/2015 | Wu ..................... A01G 7/045 47/58.1 LS |
| 2015/0313091 | A1 * | 11/2015 | Ara ..................... A01G 1/001 47/58.1 LS |
| 2016/0064204 | A1 * | 3/2016 | Greenberg ........... H01J 65/042 315/113 |

FOREIGN PATENT DOCUMENTS

| | | |
|---|---|---|
| WO | WO-2007/105946 | 9/2007 |
| WO | WO-2007/148094 | 12/2007 |
| WO | WO-2008/000306 | 1/2008 |
| WO | WO-2009/147439 | 12/2009 |
| WO | WO-2014/037852 | 3/2014 |

OTHER PUBLICATIONS

"Weeds that please" http://www.weedfarmer.com/cannabis/indoorv1_guide.php.*

"The Vaults of Erowid" https://erowid.org/plants/cannabis/cannabis_cultivation2.shtml.*

International Search Report and Written Opinion for PCT Application PCT/US2015/053309 dated Feb. 4, 2016, 8 pages.

International Search Report and Written Opinion for PCT Application PCT/US2015/053328 dated Jan. 13, 2016, 10 pages.

* cited by examiner

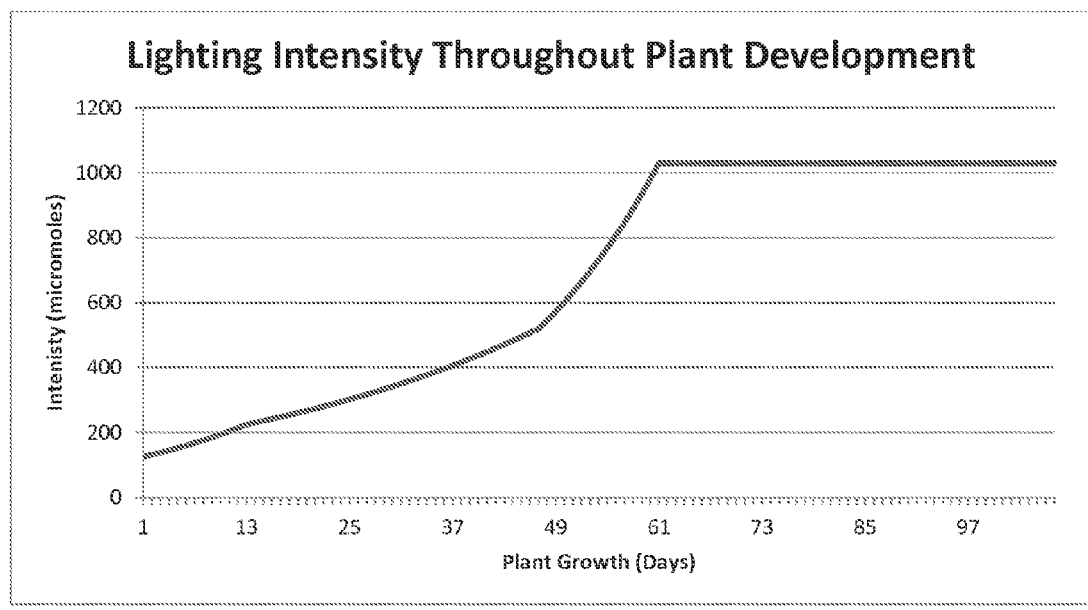

METHODS OF GROWING CANNABACEAE PLANTS USING ARTIFICIAL LIGHTING

CROSS-REFERENCE TO OTHER APPLICATIONS

This application claims priority to U.S. Provisional Application Ser. No. 62/058,045, filed Sep. 30, 2014, which is incorporated herein by reference in its entirety.

BACKGROUND OF THE INVENTION

Plants of the family Cannabaceae possess commercial value and have many uses and applications which arise from the natural products that are extracted from their flowers. For instance, hops are extracted from the flowers of *humulus* plants in this family. Hemp has multiple uses, including food and as a fiber for making clothing, rope, etc. *Cannabis* plants have long been considered to have medicinal properties. Many states, such as Colorado, Washington, Oregon, California, Alaska, Maine, Hawaii, Nevada, Vermont, Montana, Rhode Island, New Mexico, Michigan and New Jersey, allow the use of medicinal *cannabis* by persons with debilitating medical conditions as certified by physicians.

Cannabinoids, which are compounds derived from *cannabis*, are a group of chemicals from *Cannabis sativa* or *Cannabis indica* plants that are known to activate cannabinoid receptors (i.e., CB1 and CB2) in cells. There are at least 85 different cannabinoids that can be isolated from *cannabis*. These chemicals are also produced endogenously in humans and other animals and are termed endocannabinoids. Synthetic cannabinoids are man-made chemicals with the same structure as plant cannabinoids or endocannabinoids. Cannabinoids are cyclic molecules exhibiting particular properties such as the ability to easily cross the blood-brain barrier, weak toxicity, and few side-effects. The most notable cannabinoids are $\Delta 9$-Tetrahydrocannabinol (i.e., THC) and cannabidiol (i.e., CBD).

Some of the medical benefits attributable to one or more of the cannabinoids isolated from *cannabis* include treatment of pain, nausea, AIDS-related weight loss and wasting, multiple sclerosis, allergies, infection, depression, migraine, bipolar disorders, hypertension, post-stroke neuroprotection, epilepsy, fibromyalgia, as well as inhibition of tumor growth, angiogenesis and metastasis. Studies have shown that cannabinoids may also be useful for treating conditions, such as glaucoma, Parkinson's disease, Huntington's disease, migraines, inflammation, Crohn's disease, dystonia, rheumatoid arthritis, emesis due to chemotherapy, inflammatory bowel disease, atherosclerosis, posttraumatic stress disorder, cardiac reperfusion injury, prostate carcinoma, and Alzheimer's disease. For example, U.S. Pat. No. 6,630,507 discloses Cannabinoids for use as anti-oxidants and neuroprotectants; U.S. Pat. No. 7,105,685 discloses Cannabinoids for the treatment of diseases associated with immune dysfunction, particularly HIV disease and neoplastic disorders; U.S. Pat. No. 7,109,245 discloses Cannabinoids useful as vasoconstrictors; U.S. Patent Publication No. US2011/0257256 discloses THC-CBD composition for use in treating or preventing Cognitive Impairment and Dementia; PCT Publication No. WO/2009/147439 discloses use of cannabinoids in the manufacture of a medicament for use in the treatment of cancer, in particular the glioma tumor; PCT Publication No. WO/2007/148094 discloses use of cannabinoids composition for the treatment of neuropathic pain; and U.S. Patent Publication No. US2010/0286098 discloses a method of treating tissue injury in a patient with colitis administering the cannabinoids.

While such a wide range of medical uses have been identified, the benefits achieved by cannabinoids for a particular disease or condition are believed to be attributable to a subgroup of cannabinoids or to individual cannabinoids. That is to say that different subgroups or single cannabinoids have beneficial effects on certain conditions, while other subgroups or individual cannabinoids have beneficial effects on other conditions. For example, THC is the main psychoactive cannabinoid produced by the *Cannabis* species and is well characterized for its biological activity and potential therapeutic application in a broad spectrum of diseases. CBD, another major constituent of cannabinoids, acts as an inverse agonist of the CB1 and CB2 cannabinoid receptors. CBD is a phytocannabinoid which, unlike THC, does not produce a psychoactive effects in humans. CBD is reported to exert analgesic, antioxidant, anti-inflammatory, and immunomodulatory effects.

To date, however, medicinal marijuana is used as a generic product whereby the patient is utilizing the entirety of the different cannabinoids to achieve medicinal results. Efforts have been made to maximize the medicinal benefit of *cannabis* for a patient having a particular condition, but such efforts are invariably complicated. For example, *cannabis* employed by a patient lacks consistent cannabinoid components and concentrations, and thereby fails to provide the maximum benefit to the patient.

Traditional cultivation methods for Cannabaceae plants are based upon large-scale facility greenhouses with automatic watering arrangements and hydroponics like cultivation channels to achieve automatically controlled cultivation management. Such cultivation facilities generally employ an infrared light filter of natural sunlight and various mechanical devices to facilitate the management of plant cultivation. As a result, the overall cost of production is extremely high, and the success rate of actual cultivation of a desirable *cannabis* plant which reproducibly expresses certain cannabinoid components is difficult, if not impossible to control. In addition, the traditional cultivation methods for *cannabis* plants can result in problems in ineffective operations management when different *cannabis* plants at different growth stages are cultivated in the same space.

Traditional cultivation methods for *cannabis* and other members of the Cannabaceae family cannot provide consistent cultivation conditions such that the desired products are reproducibly and optimally expressed from the same strain of plant. Thus, there is an unmet need to provide methods for cultivating Cannabaceae under controlled conditions to ensure increased productivity and quality, to provide reproducible expression and production of the desired natural products, while at the same time further enhancing the technology and value of large-scale cultivation of Cannabaceae. The present invention satisfies this need as addressed by the methods below.

SUMMARY OF THE INVENTION

*Cannabis* and products/preparations thereof can be used to treat a variety of medical conditions in patients. However, the effectiveness of a given *cannabis* strain or cultivar in the treatment of a certain medical condition or symptom is dependent on the type(s) of cannabinoids and other products (e.g., terpenes) present in the cultivar, strain, or preparation, both with respect to the amount of a given cannabinoid (or terpene) and the ratios thereof. Cannabinoid compound yield and concentrations are dependent on a number of factors, including cultivar or strain type (e.g., genetic background), nutrients given, exposure to light, growth environment, harvest conditions, and methods of preparation.

This invention is directed to ensuring reproducibility of, and adjusting the yield and concentration of, cannabinoids and other potentially therapeutic products (e.g., terpenes) produced from one crop to another crop of marijuana. However, the invention is also directed to ensuring the reproducibility and maximum yield of natural products from Cannabaceae plants from one crop to the next. Notwithstanding, the invention will begin with a focus on *cannabis*. In this regard, such reproducibility and controllability, in turn, relates to ensuring predictability in flowering duration, uniformity, and yield potential. Many morphological characteristics heavily influence growth characteristics of *cannabis* plants. These growth characteristics play a role in how *cannabis* cultivars compete with one another for space, light, water, and other resources.

This invention is predicated, in part, on the discovery that, when cultivars of similar growth characteristics are exposed to a given intensity light, for the same duration in a cultivation area, the reproducibility of each generation of crop is significantly enhanced as are yields. Still further, growth environments are better utilized, pest and disease risk is decreased, and therapeutic compositions (e.g., cannabinoids, terpenes) are tunable.

In general, this invention relates to a method of cultivating *cannabis* wherein the exposure of the plant(s) to light of different intensities as said plant(s) mature will serve to acclimate said plant(s) to a light intensity necessary for optimal growth and potential. The inventors discovered that the novel lighting described herein apply to plants of the Cannabaceae family. It was found that *humulus* plants produced hopps flowers remarkably well under these artificial lighting conditions. *Cannabis* plants produced enhanced cannabinoid-laiden flowers as well. *Celtis* plants produce smaller flowers but also produce edible fruit, though it is contemplated that these lighting conditions will not affect the content of the fruit these plants produce.

The method according to the present invention provides for a precise, reproducible means of controlling the production of cannabinoid and/or terpene compounds of the plant. Desired characteristics of the plant are adjusted by altering light intensity, timing of the change in lighting intensity, and the residence time of the plant(s) exposed to each intensity level. This means of signal feedback with the plant is used in concert with the many other conditions that the grower supplies the plant. For instance, watering and nutrient supply obviously plays a large role in *cannabis* plant development. It was found by the inventors that irrigation frequency (and duration) could be varied in concert with adjustments in lighting intensity and the nutrients administered at different stages of *cannabis* plant's lifecycle to affect an increase in cannabinoid to THC ratio and overall cannabinoid yield. The use of a capillary mat to deliver both water and nutrients (e.g., fertilizer) to the plants provides additional improvement in the cultivation of the plants. It was further found that specific cannabinoid compounds could be favored according to adjustments with the lighting intensity and duration of light in several stages of *cannabis* plant development.

In one embodiment, the invention proceeds utilizing growing techniques that are well-known in the art. One skilled in the art of growing and cultivating plants will immediately recognize how to set up and use the cultivating and lighting techniques described herein. That is to say, ordinary processes and useful materials in the art such as capillary mats, plant potting systems, growing trays and/or liners, lamp fixtures, soil additives, and irrigation ductwork are within the purview of the skilled artisan. Herein the inventors have discovered how to advantageously manipulate certain signals from the plant utilizing these techniques and have thus observed *cannabis* plants participating in a novel feedback loop.

The present invention further proceeds by the development of and continued improvement and/or experimentation with a temporal lighting model for the *cannabis* plants. The skilled artisan should monitor, preferably continually, the *cannabis* plants for the leaf and stem quality, height, stem diameter, foliage spread (diameter) or evenness, and the relative % weight of certain individual(s), or in general all plants that are being cultivated at a given growth stage in this process. Such monitoring techniques are known to those skilled in the art. In this regard, samples have been taken during one or more stages of the plant life-cycle. These representative samples are then analyzed for cannabinoid content after extraction into a suitable solvent and by, for example, gas chromatography techniques. Other such analytical techniques for these purposes include plots of cannabinoid yield or average flower size, after harvest, and are within the purview of the skilled artisan, such as has been reported in journal articles and patent literature.

When developing a comprehensive cultivation model, lighting directs the plant toward optimal growth. The inventors have found that incremental increases in lighting intensity acclimate the plant to the stress which comes from the large amount of metabolic work the plant will do in the vegetative stage and first twenty (20) days of the flowering stage of development. The inventors have discovered the upper bounds of the light intensity under which optimal vegetative growth, at given points during the plant lifecycle, will produce the utmost cannabinoid yield. Further, this method of growth promote reproducibility amongst the identity and relative ratio of cannabinoids and/or terpenes produced. For example, if a given strain of *cannabis* plants has been propagated to produce a very low content of tetrahydrocannabinol (THC), this lighting technique is observed to encourage the lowest amount of THC that the particular strain is genetically programmed to produce. Moreover, this amount of THC is found to be very consistent from plant to plant and from batch to batch of *cannabis* plants grown in the same room or under these same cultivation conditions. Strikingly, this lighting technique also encourages the same cannabinoid profile amongst plants of a given strain. Particularly, the ratio of cannabidiol (CBD) to THC is found to be nearly identical amongst plants of the same strain. Further, the inventors have discovered that the plant responds most favorably to a gradual increase in the amount of light and the light intensity from early on in the vegetative stage until about twenty days after starting the flowering stage.

In one aspect, the inventors have produced a novel cultivation model for plants of the Roscea family wherein the lighting parameters dictate a great many cultivation decisions, eg. plant spacing, environmental humidity level, irrigation frequency, etc. The tuning of these parameters and their incorporation into a cultivation plan will result in dramatic increases in yield potential, cultivar availability, and an accurate prediction of yield based on several measurable/known characteristics; as well as an optimized uniformity and maximize quality in any given strain/cultivar. The invention herein provides a unique, replicable competitive advantage to increase product content from plants of the Roscea family.

A further aspect, the current invention relates to cultivation of a selected cultivar(s). Uniform lighting parameters between batches of the same cultivar allows for substantially the same cannabinoid composition (eg. CBD to THC ratio) to be obtained from the same cultivar, regardless of the batch. Moreover, certain specific cannabinoids may be favored in terms of concentration with respect to overall cannabinoid composition that is produced by the plant.

In a further aspect, the current invention relates to adjusting certain cultivation parameters in coordination with adjusting light intensity in order to repair the plant. Cultivation parameters include, for example and without limitation, fertilizer timing, fertilizer composition, watering schedules, watering quantity, nutrient content and/or concentration delivered by capillary mat and/or other irrigation systems, the amount of growth media, container size used, propagation methods, harvesting protocols, carbon dioxide concentrations, etc. Other considerations include water quality, pruning, plant support (e.g., trellising), pesticides and pest management, repotting, drying/curing, product storage, and the like.

In a general aspect, the present invention is directed to a method for increasing relative percent yield of cannabinoid compounds from a marijuana crop, the method comprises selecting at least one *cannabis* cultivar based on relative percent cannabinoid and/or terpene content, yield potential, flowering cycle, and/or certain cannabinoid composition (e.g., ratio), growing said cultivar under artificial lighting conditions to produce a specific cannabinoid and/or terpene composition, harvesting the cannabinoids based on the flowering cycle, and adjusting one or more cultivating parameters such as adjusting the growing conditions to increase the relative yield of a specific, desired cannabinoid and/or terpene compound (e.g., cannabidiol). In some embodiments, conditions include providing similar quantities of water, carbon dioxide, and nutrients to each of said cultivars.

In some embodiments, a third batch is propagated 8 to 12 days before harvesting the first batch. In some embodiments, the method is repeated in a continuous manner, such that a cultivation facility has plants at all stages of development at any given time point. That is, there is a continuous rotation of the crop, with multiple discrete batches of plants, each of which is at a given stage of the life cycle (e.g., propagation, vegetative, flowering, harvest, etc.). In some embodiments, the cannabinoid composition of the harvested *cannabis* is substantially the same in each batch. In some embodiments, the cannabinoid composition of the harvested *cannabis* is adjusted to be different in each batch. In some embodiments, the terpene composition of the harvested *cannabis* is adjusted to be different in each batch.

In some embodiments, the selected cultivar has a flowering cycle of about 56 days or about 60 days. In some embodiments, the selected cultivar has a flowering cycle of about 56 days. In some embodiments, when the cultivar has a flowering cycle of about 56 days, a batch is harvested every 8 days. In some embodiments, the selected cultivar has a flowering cycle of about 60 days. In some embodiments, when the cultivar has a flowering cycle of about 60 days, a batch is harvested every 10 or 12 days. In some embodiments, when the cultivar has a flowering cycle of about 60 days, a batch is harvested every 10 days. In some embodiments, when the cultivar has a flowering cycle of about 60 days, a batch is harvested every 12 days. In some embodiments, a batch is harvested based on square footage.

In some embodiments, the selected cultivar is allocated to a cultivation facility based on flowering cycle, such that all of the cultivars at the facility have the same flowering cycle.

In some embodiments, two or more cultivars are selected. In some embodiments, the cultivars are grouped based on at least one morphological characteristic, such that cultivars with the same characteristics are grouped together. In some embodiments, two or more cultivars are used to sexually reproduce a desired strain. In some embodiments, the morphological characteristic is based on height. In some embodiments, the morphological characteristic is based on canopy circumference.

BRIEF DESCRIPTION OF THE DRAWINGS

FIG. 1 depicts an exemplary graph of artificial lighting intensity being increased gradually from the initial cutting, propagation of a Clone until its harvest as a fully mature, flowered *cannabis* plant.

DETAILED DESCRIPTION

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

Definitions

It must be noted that as used herein and in the appended claims, the singular forms "a", "an", and "the" include plural referents unless the context clearly dictates otherwise. Thus, for example, reference to "a compound" includes a plurality of compounds.

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 10%, 5% or 1%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

"*Cannabis*," "*cannabis* species," or "marijuana" refers to a flowering plant including the species (or sub-species) *Cannabis sativa*, *Cannabis ruderalis*, and *Cannabis indica*.

"Cannabinoids" refers to a class of chemical compounds that act on the cannabinoid receptors. "Endocannabinoids" are produced naturally in animals, including humans. "Phytocannabinoids" are naturally-occurring cannabinoids produced in plants. "Synthetic cannabinoids" are artificially manufactured cannabinoids.

*Cannabis* species express at least 85 different phytocannabinoids, which are concentrated in resin produced in glandular trichomes. The phytocannabinoids are divided into subclasses based on, including cannabigerols, cannabichromenes, cannabidiols, tetrahydrocannabinols, cannabinols and cannabinodiols, and other cannabinoids.

Cannabinoids found in *cannabis* include, without limitation: cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabinolic acid (THCA), and tetrahydrocannabivarinic acid (THCVA). Phytocannabinoids and their structures are discussed in more detail in U.S. Patent Application Pub. No. 2013/0059018, which is incorporated herein by reference in its entirety.

Phytocannabinoids can occur as either the pentyl (5 carbon atoms) or propyl (3 carbon atoms) variant. The propyl and pentyl variants may have distinct properties from one another. For example, THC is a CB1 receptor agonist, whereas the propyl variant THCV is a CB1 receptor antagonist meaning that it has almost opposite effects from THC.

"*Cannabis* components" include any therapeutic or potentially therapeutic compounds produced by or found in the *cannabis* plant and/or products thereof. *Cannabis* components include, but are not limited to, cannabinoids and terpenes.

"Products of *cannabis*" as used herein refers to any products derived from the *cannabis* plant, including but not limited to the flower, resin (hashish), and oil (hash oil), as well as any preparations thereof. Preparations include, by way of non-limiting example, dried flower, kief, hashish, tincture, hash oil, infusions, pipe resins, edibles, and the like.

"Clone" refers to a plantlet cutting that is removed from another, healthy *cannabis* plant. Tissue is collected from the stem and shoot sections of the healthy *cannabis* plant, and generally consists of at least (3-4) nodes and one apical meristem.

"Yield potential" as used herein refers to the grams of product per square foot of cultivation space expected to be generated by a given *cannabis* strain or cultivar over a period of time. In a preferred embodiment, the period of time is the time from propagation to harvest of a *cannabis* plant or batch.

The term "life cycle" as used herein refers to the progression of a plant through various stages of growth. *Cannabis* plants go through a vegetative stage of growth, followed by a flowering cycle. The period of growth between germination or cutting rooting and flowering is known as the vegetative phase of plant development. Vegetation is the sporophytic state of the *Cannabis* plant. Plants do not produce resin or flowers during the vegetative stage and are bulking up to a desired production size for flowering. During the vegetative phase, plants are busy carrying out photosynthesis and accumulating resources that will be needed for flowering and reproduction.

"Flowering cycle" or "flowering phase" (also called "bud cycle") refers to the period during which the plant produces buds and flowers. This is the reproductive phase of plant growth. *Cannabis* is dioecious, having female and male reproduction parts on separate plants. Flowering is the gametophytic or reproductive state of *Cannabis*. For production, only female flowers are selected for cultivation. For some cultivars, the switch from the vegetative stage to the flowering stage is light-dependent. Some cultivars are auto-flowering, meaning they switch to the flowering stage automatically (e.g., with age).

"Vegetation cycle" or "vegetative phase" refers to the period of growth between germination or cutting rooting. Vegetation is the sporophytic state of the *cannabis* plant. This is a form of asexual reproduction in plants during which plants do not produce resin or flowers. The plant is bulking up biomass to a desired production size for flowering. During the vegetative phase, plants are busy carrying out photosynthesis and accumulating resources that will be needed for flowering and reproduction.

"*Cannabis* cultivar" and "*cannabis* strain" are used interchangeably herein, and refer to *cannabis* plants that have been selected for one or more desirable characteristics and propagated. Where the term cultivar or strain is used, it is to be understood that the cultivar or strain may be naturally-occurring, a result of breeding, and/or the result of genetic manipulation. Propagation may occur in any manner, including, without limitation, sexual reproduction (e.g., seed), cloning (e.g., cuttings, vegetative propagation), self-pollinization, and the like.

A "plurality" as used herein refers to more than one. For example, a plurality of cultivars may be two, three, four, five, or more cultivars.

"Plants of the family Cannabaceae" as used herein refers to any member of the Cannabaceae family of plant organisms including, but not limited to, *Celtis, Cannabis*, and *Humulus* plants.

The term "artificial lighting" as used herein, refers to any light or apparatus that generates light for the growth and development of a plant.

The term "shoots" as used herein, refers to the parts of the plant including the stem, any and all appendages, leaves, lateral buds, flowering stems, and flower buds.

The term "node" as used herein, refers to the point on a plant stem from which the leaves or lateral branches grow.

General Cultivation Methodology Used in Cooperation with the Lighting Technology
Cultivar Specificity Even minor differences in environment between cultivars result in differences in the final cannabinoid and/or terpene composition. In one aspect of the present invention, each cultivar is segregated, meaning that square footage is dedicated to a given cultivar only at a single location. This maximizes the genetic diversity one *cannabis* cultivator can supply and maximizes the efficiency of lighting between cultivars. Through this process, the genetic diversity at one location can be minimized while maximizing uniform Cannabaceae plant growth under these lighting conditions.

Grouping of Cannabaceae cultivars based on their morphological characteristics increases the yield, uniformity, and quality of both the canopy and product (e.g., flower) by maximizing resource utilization. Also, by plotting the specific quantities of each cultivar, a cultivation facility can more accurately predict yields.

In one embodiment, a specific cultivar is administered differing concentrations of nutrients via capillary mats in response to growth by the plant under specific intensity of light. In another embodiment, certain selected, high-yield potential cultivars are administered a lower concentration of nitrogen-containing nutrient via a capillary mat in response to increase intensity in the middle to late stages of vegetative phase of growth, and thus with increased height of the plant. In other embodiments, other selected cultivars are administered nutrient content that initially increase quickly and then decrease gradually over time with artificial lighting of the plant.

Crop Scheduling

Through the implementation of the crop scheduling and establishment of stages of growth as encompassed by the current invention, perpetual cultivation cycles can be established. These strict, perpetual cultivation cycles allow for continuous flowering schedules that maximize specific and overall cannabinoid yield potential. In one embodiment, perpetual cultivation cycles are established by growing *cannabis* in batches. In one embodiment, when a first batch progresses from a first stage of growth to a second stage of growth, a subsequent batch progresses into the first stage of growth. In one embodiment, a third batch is propagated about 8 days to about 12 days before harvesting the first batch. As such, in exemplary batch schedules, wherein as one batch transitions from a first stage into a second stage, a subsequent batch transitions into the first stage (e.g., is propagated) and a previous batch transitions to a third stage from the second stage, etc. As would be understood by one of skill in the art, the schedules explained are merely examples of potential cultivation schedules, and more or fewer stages, different stages, different timings and durations, more or fewer batches, and the like may be utilized.

Dependent on the cultivation method, production schedules are established on 56 day flower durations or 60 day flower durations. This requires that all the flowering cultivation square footage is harvested every 56 days or 60 days, and generally, this square footage is incrementally harvested in evenly divisible durations based on bench square footage. These substituent harvests are referred to as 'batches'.

In some embodiments, cultivars with 56 day flower cycles are harvested every 8 days, requiring 7 batches. In some embodiments, cultivars with 60 day flower cycles are harvested either every 10 days or every 12 days, requiring 6 or 5 batches, respectively. On the $56^{th}$ or $60^{th}$ flowering day in its entirety, a batch is harvested and the next vegetative batch is immediately transitioned into flower. The last day of flower for one batch is the first day of flower for the next batch. In some embodiments, this process maximizes the profitability by not allowing production square footage to go unoccupied.

By adhering to longer flowering cycles, typical cultivation operations achieve approximately 4 harvests per year. In some embodiments, by utilizing the lighting techniques of the present invention, cultivation methods based on 56 day flower cycles achieve 6.52 harvests per year. In some embodiments, by utilizing the techniques of the present invention, cultivation methods based on 60 day flower cycles achieve 6.08 harvests per year. In one aspect, the invention then improves overall energy efficiency in terms of cultivation by maximizing time, space, and lighting parameters which produce the maximum yield of product.

The number of vegetative stages of growth and frequency of cloning can be predetermined based on flowering cycle determination. Establishing defined stages of growth allows for maximization of plant health, size, square foot capture, and optimization of resources.

In one embodiment, the flowering cycle duration also determines the frequency at which new batches should be propagated. Using methods of the present invention, Clones root within 8-12 days. In order to have a plant stock immediately available to occupy vegetative square footage emptied by harvesting a previous batch, propagation should occur 8-12 days before each harvest.

In containerized plants, nursery and greenhouse standards recommend one gallon of soil per month of cultivation. The number of stages of vegetative growth and total vegetative square footage determines the number of vegetative stages over the life cycle of the cultivar. With strict, predetermined timing of vegetative stages established, the frequency of propagation can be scheduled, and the container size used to hold the media and provide plant support can be calculated. For example, a cultivation facility growing cultivar(s) with a 60-day flower cycle and utilizing six batches may have vegetative square footage that allows for 40 days of vegetative growth and four stages of growth. This cultivation cycle in its entirety is 100 days, requiring a four gallon container (100 days/30 days/month=3.54 gallons). In one embodiment of the invention, optimization of vegetative stages of growth and container volume results in increased cultivation probability, uniformity and yield potential.

Utilizing strict propagation, vegetative, and flowering schedules allows for cultivation resources to be used to their highest potential, thereby increasing product yield. By exploiting all the available vegetative time, *cannabis* cultivars are better able to utilize resources to produce high-quality product. This increases yield potential predictability through ensuring that all usable square footage is occupied with foliage. In addition, profitability is increased by capturing cultivation resources and square footage.

Cultivation Parameters in Cooperation with Lighting Duration

Clone Room

In the Clone room, the temperature is to remain between 68-74° Fahrenheit. Leaf temperatures are to be between 68-73° Fahrenheit. The ideal humidity is dependent on the leaf temperature and vapor pressure gradient but generally is between 80-90% relative humidity. The humidity needs to be high enough to cut transpiration rates so that wilting doesn't occur. The lighting schedule is generally 18 hours of light and 6 hours of darkness or 24 hours of continuous light. During this time, there is to be no carbon dioxide treatment.

Vegetative Stock Room

In the Vegetation room, the temperature is to remain between 74-80° Fahrenheit. The leaf temperatures are to be between 76-80° Fahrenheit. The ideal humidity is dependent on the leaf temperature and vapor pressure gradient but generally is between 50-60% relative humidity. The lighting schedule is generally 18 hours of light and 6 hours of darkness or 24 hours of continuous light.

Flower Room

The temperature in the flower room is to remain between 73-78° Fahrenheit. The leaf temperatures are to be between 72-77° Fahrenheit. The ideal humidity is dependent on the leaf temperature and vapor pressure gradient but generally is between 45-55% relative humidity. In one embodiment, the lighting schedule is 12 hours of light and 12 hours of darkness.

Lighting Methodology

Overall, this invention relates to a method of controlling the cannabinoid production of a *cannabis* plant, wherein the use of artificial lighting of different intensity during different growth stages serves as a means for signaling the plant to adjust its metabolism, and thus its cannabinoid production during its lifecycle. The technique, as such, can be thought of as a feedback loop between the plant and grower. In this regard, the invention includes a number of illustrative, but certainly not limiting, examples of certain variables that are adjusted (in concert with lighting intensity) in order to increase cannabinoid production from the *cannabis* plant. These variables include, but are not limited to: specific and individual cultivar selection, lighting characteristics, carbon dioxide treatment, pesticide treatment, growth medium size and content, time and environmental conditions in growth cycle, nutrient treatment, and any optionally additional irrigation of the plant.

Light Utilization

The physics of light distribution in artificial environments and biological processes related to plant-light interactions play important roles in plant growth and yield. By incorporating several lighting concepts, a given plant's growth potential is realized, product yield and product efficiency increases markedly, the total whole flower produced increases, and flower uniformity becomes achievable. The invention uses these concepts in conjunction with multiple other different horticulture technologies (e.g., capillary mat irrigation). This technology provides numerous benefits to commercial and private cultivation of members of the Roscea family of plants. Optimizing the artificial light absorbed during the vegetative and flowering stages increases the quality of individual *cannabis* flowers, absolute yield (g/sqft), and yield efficiency (g/watt).

Background: Complete artificially illuminated cultivation is not practiced in the production of most plants. The additional cost associated with the operation of high-intensity discharge (HID) lighting fixtures prohibits commercial cultivation of most plants. Though in research applications, energy consumption is seldom considered. In such cases, horticulturists set the intensity value illuminated usually at a fixed value in order to simulate daylight. The inventors have discovered, however, that energy, in this scenario, is over-consumed.

Surprisingly, this over-consumption is a detriment to some plants. Specifically, the inventors found that plants from Cannabaceae family produce more biomass, more efficiently, under lighting conditions that consider plant maturity and acclimation to the coming metabolic stresses. Through many arduous experiments, the inventors found that a gradual increase, from about 1 to about 5%, in the intensity of light, for each succeeding stage of vegetative growth will produce the optimal growth from the plant. In particular, *cannabis* plants seemed to respond spectacularly to this sort of ramp up in lighting intensity in the vegetative stage until about the $15^{th}$ day of flowering. At this time, *cannabis* plants in particular had achieved sufficient acclimation to the metabolic stress the plants need for optimal flower and product yield.

Light and Plant Spacing

The methods of the invention also consider the interaction between space and light. In practice, because of reflection and other phenomena, artificial lighting does not provide an even distribution of light intensity over a given area. In order to overcome this problem, the invention also provides for movement of the plant or the lighting fixture in order to obtain an even light absorption of any one given plant. This movement aspect increases the efficiency of the methodology at converting electrical energy into usable yield. Further, this enables cultivation from batch to batch to become highly reproducible. By utilizing move-able platforms (e.g., rolling-top benches), plants occupying bench space have the intensity of light distributed throughout the crop canopy. By distributing the intensity throughout the plant canopy, a more even plant growth is obtained. This improves plant quality in vegetative growth, flower uniformity, and the percentage of high quality flowers per pound of total product. Spreading the same amount of light over additional bench space and plants will yield improvements in both absolute yield and yield efficiency.

The inventors have discovered that artificial fixtures may be mounted, during the flower phase of growth, to provide continuous lighting to an area at 500-1100 micromoles $(m^{-2}s^{-1})$. It is important to note that this not restricted to the platform or bench-top upon which the plant is held. Instead, both bench-top spaces and aisles are illuminated. Move-able platforms which hold the plants may or may not be evenly spaced across the illuminated area in order to form a continuous canopy. The cultivator may bias one side, creating an uneven spacing with an excess number of plants for cases when some plants need time under that intensity of artificial light. Such cases allow the cultivator to place slightly younger and older plants on the same platform. Nevertheless, the three-dimensional nature of this crop occupies the additional space, allowing aisles to produce additional yield. By illuminating this extra area, the total volume of canopy illuminated increases, and by extension, total amount of product produced increases.

Light Quality

Another important consideration is light quality. Light quality, also referred to as spectral distribution, is the quantity of photons at each wavelength of light (color) produced by a particular light source. The light quality produced by the light source has numerous effects on plant growth and morphology.

Background: The lighting quality produced by the light source(s) influences the energy efficiency of the light source for plant growth, the amount of light available for growth, and plant temperatures (an important aspect of plant physiology). When a high percentage of the wavelengths of light emitted by the source are useful for plant growth, cooler plant temperatures result and greater energy efficiency is realized. Light sources that produce non-useful wavelength contribute to greater plant temperatures, as plant pigments absorb and reemit this light energy as heat. Lamps that produce these non-useful wavelengths also tend to have lower efficiency at converting electrical energy into light that is useful for plant growth, so they typically require more watts of energy per unit area to achieve target lighting values for that stage of growth.

Plant pigments only absorb certain wavelengths of light, so the total quantity of photons produced by the light source is not as important as the quantity of photons in certain wavelengths. Photons in the range of 400-700 nm are productive wavelengths of light which contribute to photosynthesis and growth. However, the photons produced in certain regions within this range contribute, in varying degrees, to photosynthesis and growth. Blue light (450-500 nm) will inhibit the production plant hormones responsible for stem elongation (Gibberellins). A decreased red and/or far red light (620-750 nm) to blue light ratio will promote the elongation of stems. The inventors have found this ratio to ideally be within the range from about 1:5 to about 1:10 (blue light relative to red light produced by the fixture) in order to maximize the growth potential of the plant.

Further, the absolute amount of photons in these ranges play a large role in how flower sites are positioned along a stem (internode length). The effect of which on yield is as follows. Light intensity refers to the amount of photons within the photosynthetically active radiation (PAR) range (400-700 nm) that strike a given area per unit time. It is typically referred to as photosynthetic photon flux density (PPFD) and is quantified in micromoles per meter squared per second ($\mu mol \cdot m^{-2} s^{-1}$). As light intensity (thus more photons) is increased, plant growth increases. This trend continues throughout growth stages of the plant until a certain value is reached where light intensity is increased and no increases in growth will result. This point is called the light saturation point. The light saturation point of an individual leaf (or plant) depends on multiple factors: plant age, acclimation processes, variety, and microenvironment. The inventors have discovered that plants of Cannabaceae family, when grown at high light intensity, have: smaller, thicker leaves; more chlorophyll; higher light saturation points; and higher light compensation points. Accordingly, the same plant, grown in low intensity light conditions will have: thinner, larger leaves; less chlorophyll; lower light saturation points; and lower light compensation points. Since these plants have been found to have growth and yield increases with increasing light intensity, it has been found and is therefore advantageous to develop a vegetative plant that is acclimated to higher light intensity. The inventors have demonstrated that the longest amount of time these plants tolerate between acclimation events is around five (5) days. The inventors, working backward from this discovery, then experimentally determined that anywhere between a 1-10% increase in the light intensity provided (the increase being measured as a percentage of the total intensity of light currently provided) on a daily basis is optimal in order to achieve the maximum potential growth of the plant. This aspect of the invention ensures that the plant will endure less stress in its transition to flowering; and will be able to produce more growth from the available light in flowering areas. Thus, the inventors have also found that placing plants which are adapted to lower light intensity into flowering areas has several negative effects including: increased plants stress, reduced growth, and nutritional deficiencies (e.g., potassium, magnesium).

Light Penetration

The penetration of these wavelengths of light will affect how light is distributed throughout the plant canopy. Photon distribution is affected by such variables as: reflector type, lighting source type, mounting height, etc. However, light penetration also refers to how much the distribution of light occurs in a vertical axis. This is influenced heavily by the mounting height. Light sources that produce a large quantity of light per fixture, or have a high penetration reflector, tend to have a larger mounting height, and light diminishes less rapidly per inch as you move vertically down into the plant canopy. Fixtures with smaller wattages, and/or reflectors with large distribution patterns, typically diminish at a much larger rate on a vertical axis, but tend to have higher degrees of uniformity in its distribution of intensity across the plant canopy on a horizontal axis. These lighting fixtures tend to minimize the amount of space needed for any given plant, though, at the expense of growing shoots lower in height and therefore more overall flowers. Finding the correct balance between these two strategies is very important in growing Cannabaceae plants during the flower stages.

Light Acclimation:

One challenge in this acclimation process is developing these plants, which are rooted at low light intensities, and gradually increasing light intensity while simultaneously avoiding light stress. The inventors have discovered that by increasing light intensity from 1-10% of the total light intensity currently given, the potential growth is maximized while light stress is minimized. Moreover, it was determined that this methodology allows for using the smallest amount of physical space for vegetative growth, and thus is more efficient method in terms of light required, space allocated, and yield produced by the these plants.

Guidelines for the Lighting Methodology

In one aspect, the invention provides for the following ranges of light intensity at each corresponding growth stage and plant density in order to provide a maximum yield from any given plant in the batch:

1) Newly-cut, Clone stage 1: 105-165 micromoles $m^{-2} s^{-1}$, up to 7 days from cutting
2) Clone stage 2: 'Hardening'-150-215 micromoles $m^{-2} s^{-1}$, 7-13 days from cutting
3) Vegetative Stage 1: 200-270 micromoles $m^{-2} s^{-1}$, through day 10-21 after transplant, 0.23-0.38 sqft/plant
4) Vegetative Stage 2: 260-350 micromoles $m^{-2} s^{-1}$, through day 20-31 after transplant, 0.51-0.86 sqft/plant
5) Vegetative Stage 3: 320-500 micromoles $m^{-2} s^{-1}$, through day 30-46 after transplant, 0.93-1.57 sqft/plant
6) Newly initiated flowering plant: 450-1100 micromoles $m^{-2} s^{-1}$, through day 1-20 of flower, 3.95-5.95 sqft/plant
7) Mid flower until harvest: 950-1100 micromoles $m^{-2} s^{-1}$, day 20 through the end of flower, 3.95-5.95 sqft/plant Of course, these are general guidelines for the intensity a plant should be exposed to during a particular point of maturation. The invention also includes a much shorter vegetation period. In such scenarios, there may be three vegetative phases each lasting a smaller number of days. Accordingly, a cultivator will need to increase the intensity in a much larger fashion, ramping up more quickly to about the desired 500 micromoles of light intensity that ought to be targeted in order to move the plant into the flowering phase. If the time constraints, due in part to number of problems the plant may experience, do not feasibly allow the cultivator to acclimate the plant to about 500 micromoles by the end of vegetation (if say the % increase in intensity were untenable and perhaps as much as 70%), then the cultivator would try to spread the increase in light into the flowering phase and acclimate the plant accordingly. Thus, common cultivation cases could be as low as a 30-35 day vegetative phase. Any less than this and the cultivator must start moving the acclimation period into the flowering phase, as mentioned.

During each stage, the light intensity is increased over the duration of the stage by small increments (e.g., about 1% to about 10%) every one to seven days.

Selection and Placement of Artificial Light Technology

In one aspect, the lighting source used is dependent on the stage of growth. Lighting sources that produce larger amounts of photons in the PAR range, a greater degree of light penetration, and warmer color temperature lamps are typically utilized in the flower phase. This is due to the fact that the yield (and quality) of an individual flower is highly dependent on the micro-environment of that flower.

The inventors have found that in vegetative growth phases, the required characteristics needed for an artificial lighting source differs compared to flowering requirements. Typically, plants are much shorter in height, so a large degree of light penetration is not needed. Since plants are shorter, there is not a large difference in intensity from top to bottom of the plant, as not enough distance elapses from the source for significant diminishment of intensity to occur.

Lighting quality and spectral distribution needs also differ between the two different production areas. During vegetative growth, a smaller, squatter plant form is desirable, as finishing height of the plant in flower is highly controlled by the finished size of the vegetative plant. Shorter, more compact plants entering flowering areas from vegetative growth may contribute to a more ideal plant height for flower production. A spectral distribution of the light including large relative amounts of blue light is highly desirable for vegetative growth stage. Without being bound by theory, it is believed that blue light suppresses internode elongation and achieves the proper growth morphology to achieve a squatter, bushier plant.

For flowering areas, a warmer color temperature lamp is typically used. This is done for several reasons. With most lighting technologies, the production of longer wavelengths of light is more energetically favorable. As such, lamps which produce greater amounts of longer wavelengths of light typically produce more total photons. Although this is not universally true for all lighting sources, this has led to the use of warm-color temperature lamps in flowering areas. The additional intensity of longer wavelength photons has a positive influence on flower production and yield.

The main challenge in flowering production is that these warmer-color temperature lamps (typically high-pressure sodium lamps; HPS) usually lead to increased internode length, due to the lack of the blue light created by the lamp. This can have detrimental effects on plant morphology. Increasing internode length increases the distance between flower sites along the stem. As the distance between flower sites increases, the variance in light intensity between these flowers increases. The diminished light intensity received by flowers in lower portions of the plant decreases the yield and quality of these flowers, and increases quality variability between flowers.

1. Early Vegetative growth (Clone & Vegetative stage 2) lamp selection: T-5 fluorescent lamps, ceramic metal halide (CMH) lamps, metal halides (MH), double ended metal halides (dMH), and light emitting diodes (LED).

2. Late Vegetative growth (stage 3 & 4) lamp selection: LED, plasma bulbs, and larger wattage MH lamps (600 watt & 1000 watt). The "burning" or color-temperature rating on these lighting sources, for the vegetative phase of growth, are generally selected to be from 4000-6000 Kelvin.

3. Flowering lamp selection: double ended HPS, certain LED.

4. Combination lighting for Flowering: double-ended HPS/LED strips (double-ended HPS overhead and LED strips are mounted to the trellis posts and optionally to the side walls, such that the canopy is illuminated with an additional 100-200 micromoles.

5. Combination lighting for Flowering: double ended HPS and plasma lights (double-ended HPS overhead and plasma bulbs (source of UV-b light) are mounted to the trellis posts and optionally to the side walls, such that the canopy is illuminated with an additional 100-200 micromoles). The "burning" or color-temperature rating on these lighting sources, for the flowering phase of growth, are generally selected to be from 1000-2500 Kelvin.

In one aspect, cultivators can optionally place LED strips, MH/dMH bulbs, and even a CMH onto supports which are near the bottom of the plant. These arragements are temporary and act to suspend the lighting source in order to expose the plant to light from the bottom upward, as opposed to from the top downward. In a similar manner, the inventors have found that mounting lighting sources such as LED strips, MH, dMH, and even double-ended HPS on the sides of growing plants will increase plant growth and thus, flower and yield.

In one embodiment, the invention relates to a method of growing a plant wherein the lighting fixture in any given area remains stationary and the plant moves when it is within any one of the lighted areas. In one embodiment, the movement is continuous.

In one embodiment, the invention relates to a method of growing a plant wherein the plant may be continuously moving on a platform, supporting the plant, which can be a conveyer belt, inline track, rolling top bench, or an equivalent thereof when it is within any one lighted areas. Such methods of moving a plant whilst providing nutrients and water are within the purview of the skilled artisan.

In one embodiment, the invention relates to a method of growing a plant wherein the lighting fixture in any given area moves, however the plant remains stationary within any one of the lighted areas. In one embodiment, the movement is continuous.

In one embodiment, the invention relates to a method of growing a plant wherein the lighting of the plant is maximized by fixtures placed on one or more of top, the sides, and the bottom of the plant.

In one embodiment, the invention relates to a method of growing a plant wherein the lighting of the plant is maximized by implementing the regimen of artificial lighting as described in this application and by placing one or more layers (e.g., 1-5, preferably 3) of trellis thru the shoots and/or foliage of one or more of the plants in order to spread the foliage of the plant out over a greater area in either a horizontal or vertical direction, or both. Further, a given layer of trellis may be added to improve evenness of the canopy of plants exposed to the lighting.

In one embodiment, the invention relates to a method of growing a plant wherein said plant is grown under, or moved to, artificially lighted areas of differing intensity of artificial light which may be adjusted based upon the height, stem thickness, and number of shoots or nodes of the plant.

In one embodiment, the invention relates to a method of growing a plant wherein said plant is exposed to artificial light in the vegetative phase for a range of about 30 days to about 60 days.

In another embodiment, the invention relates to adjusting either the lighting intensity, lighting fixture, atmospheric conditions, or the nutrient conditions in order to affect certain observable properties within a *cannabis* plant and allow harvesting at an appropriate time. While cannabinoid production is not directly controlled by varying harvest time, such significantly influences the relative ratio of THC and cannabinoids within the buds of the *cannabis* plant. The grower will make observations regarding certain characteristics of the plant, including the pistils, the trichomes, and any emanating aroma. For example, in order to increase cannabinoid to THC ratio, the grower will change a lighting fixture to another type, say from an LED to a plasma source, in order to increase an intensity of blue and UV lighting which ultimately encourages more yield. The grower will also recognize trichome changes in the plant's response. In one embodiment, the grower harvests the *cannabis* plant when the trichomes have recently changed to a slight amber color. Still further, the skilled artisan or grower will recognize that these adjustments and then subsequent responses must be timed during the plant life-cycle such that the *cannabis* plant becomes fully mature in order to carry out proper drying and curing post-harvest.

Processes Relating to Space Utilization and Light Optimization

Two critical aspects of *Cannabis* cultivation facility design and operations that heavily influence the success and profitability of 100% artificially illuminated environments are: space utilization and light optimization. These two concepts are often times related to one another. The physics of light distribution in artificial environments and biological processes related to plant-light interactions play important roles in plant growth and yield, which in turn, has a large influence on facility design aspects and operations costs.

The present invention relates several facility design concepts that incorporate these interactions into facility design to increase, for example but not limited to, plant growth, yield efficiency, total whole flower produced, and flower uniformity. These general design concepts are utilized in conjunction with multiple different lighting and horticulture technologies. These technologies provide numerous other benefits to operations, and operate synergistically and cooperatively to increase production space profitability.

By optimizing light intensity values and space in vegetative growth areas, the amount of space required to grow a particular cultivar is reduced. This increases the amount of flowering space that is available as yield-producing areas. Since less vegetative space is used, more of the facility square footage can be dedicated to flowering areas. By maximizing plant growth, shorter vegetative cycles can be used while still allowing the perpetual production of all flowering benches. By optimizing light and space in vegetative growth, the amount of energy consumed and space needed to supply flowering benches with sizeable plants is vastly reduced.

By optimizing light and space aspects in the flower room areas, several benefits are realized. The quality of individual *Cannabis* flowers, which is highly determined by the light environment of the individual flower, becomes more uniform with the implementation of these lighting and horticultural technologies. Additionally, both absolute yield (g/sqft) and yield efficiency (g/watt) are vastly improved. The unique combination of newer lighting technologies with existing greenhouse technologies applied in a systematic manner has proven to be a superior method of *Cannabis* cultivation.

The present invention is directed to technologies and processes implemented, relating to space and light optimization, 1) rolling top benches, including but not limited to, retrofit existing facilities; expand light footprint, and replacement of light movers; 2) lighting technologies, including but not limited to, acclimation processes, lamp selection, and combination lighting; and 3) rolling top benches and their utilization in one hundred percent artificially illuminated *cannabis* cultivation facilities.

Rolling Top Benches

With commercial *Cannabis* production, the interaction between space and light is increasingly important. The efficiency at converting electrical energy into usable yield, and the total amount of yield received from the space are two important aspects of completely artificially illuminated plant production areas. The use of rolling top benching is uncommon, and there are several ways in which it can be utilized to increase productivity (g/sqft, g/watt, total grams produced).

In some embodiments, "rolling top" benching is used for enhancement of yield efficiency and total product yield in one hundred percent artificially lit commercial *Cannabis* production environments. Enhancement of yield can be accomplished through multiple mechanisms, including but not limited to, utilizing rolling top benches to retrofit existing facilities; utilizing rolling top benches to increase the area of the light footprint that is able to be installed in the facility; and utilizing rolling top benching to replace "light movers."

In some embodiments, rolling top benches are utilized to retrofit existing facilities. By increasing the amount of bench space dedicated to an artificial light, more total yield and better yield efficiency per energy input is realized. The mounting height of the lighting fixture is increased to illuminate a greater area. By spreading the same amount of light over additional bench space and plants, yield improvements result (both absolute yield and yield efficiency).

In some embodiments, rolling top benches to increase the area of the light footprint that is able to be installed in the facility are utilized. Artificial fixtures are mounted to provide a continuously lit area of 650-900 micromoles $m^{-2}s^{-1}$, which is not restricted to the bench top areas. Instead, both bench top spaces and aisles are illuminated. Rolling top benches may roll into the aisles, and are evenly spaced across the illuminated area to form a continuous canopy. The three-dimensional nature of the crop occupies the additional space, allowing aisles to produce additional yield. By illuminating this extra area, the total volume of canopy illuminated increases, and by extension, total amount of product produced increases.

In some embodiments, rolling top benching to replace "light movers" are utilized. Light movers are typically used to rotate where light is focused throughout the plant canopy. By replacing the use of "light movers" with rolling top benches, similar effects are realized.

Artificially lit areas do not have even distribution of light intensity. By utilizing rolling top benches, plants occupying bench space have the intensity of light rotated throughout the crop canopy. By rotating light throughout the plant canopy, more even growth of *cannabis* is obtained. This improves plant quality in vegetative growth, and flower uniformity and the percentage of high quality flowers per pound of total product.

In some embodiments, movement of the plants is automatic. In some embodiments, automatic movement of the plants is continuous or at pre-determined intervals. In some embodiments, movement of the plants is manual. In some embodiments, the manual movement is at predetermined times, random, and/or periodic.

Lighting Technologies

There are numerous types of horticultural lighting available for 100% artificially illuminated production areas. The lighting technologies vary fairly widely in several characteristics, which alter the ways in which they can be applied to optimize plant growth and yield. The type of lighting technology, and the way in which it is utilized play an important role in: plant growth and morphology, total yield (g/sqft), yield efficiency (g/watt), and facility energy efficiency (lbs/kWh).

There are several properties of artificial light that are important considerations in its application for the production of plants: quality, intensity, and penetration. Light quality, also referred to as spectral distribution, is the quantity of photons at each wavelength of light (color) produced by a particular light source. The light quality produced by the light source has numerous effects on plant growth and morphology. Plant pigments only absorb certain wavelengths of light, so the total quantity of photons produced by the light source is not as important as the quantity of photons in certain wavelengths. Light in the range of 400-700 nm (PAR light) is productive wavelengths of light, which contribute to photosynthesis and growth. Photons produced in certain regions within this range contribute, in varying degrees, to photosynthesis and growth.

The lighting quality produced by the light source(s) influences the energy efficiency of the light source for plant growth, the amount of light available for growth, and plant temperatures (an important aspect of plant physiology). When a high percentage of the wavelengths of light emitted by the source are useful for plant growth, cooler plant temperatures result and greater energy efficiency is realized. Light sources that produce non-useful wavelength(s) contribute to greater plant temperatures, as plant pigments absorb and reemit this light energy as heat. Lamps that produce these non-useful wavelengths also tend to have lower efficiency at converting electrical energy into light that is useful for plant growth, so they typically require more watts of energy per unit area to achieve target lighting values for that stage of growth.

Light quality also has an effect on plant morphology (the form of the plant). Blue light will inhibit the production plant hormones responsible for stem elongation (e.g., Gibberellins). A low red/far red ratio will promote the elongation of stems. The relative amounts of photons in these ranges play a large role in how flower sites are positioned along a stem (internode length). The effect this has on yield will be discussed below.

In some embodiments, exemplary combinations of light and space regiment are used: Newly cut clone—105-165 micromoles $m^{-2}s^{-1}$, up to 3-6 days from cutting; Clone 'Hardening'-185-250 micromoles $m^{-2}s^{-1}$, 7-14 days from cutting; Transplant—225-285 micromoles $m^{-2}s^{-1}$, through day 7-15 after transplant, 0.23-0.38 sq ft/plant; VS2—275-300 micromoles $m^{-2}s^{-1}$, through day 14-24 after transplant, 0.51-0.86 sqft/plant; VS3—300-350 micromoles $m^{-2}s^{-1}$, through day 21-36 after transplant, 0.93-1.57 sqft/plant; VS4—350-400 micromoles $m^{-2}s^{-1}$, through day 32-48 after transplant, 1.55-2.58 sqft/plant; Newly initiated flowering plant—450-600 micromoles $m^{-2}s^{-1}$, through day 6-10, 3.95-5.95 sqft/plant; and Mid flower-harvest 700-950 micromoles $m^{-2}s^{-1}$, through the end of flower, 3.95-5.95 sqft/plant.

In some embodiments, unique artificial lighting technologies for plant growth enhancement are selected. The characteristics of the artificial lighting source can play an important role in how the particular lighting technology is best utilized in one hundred percent artificially illuminated indoor cultivation. Lighting sources that produce larger amounts of photons in the PAR range, a greater degree of light penetration, and warmer color temperature lamps are typically utilized in flower. This is due to the fact that the yield (and quality) of an individual flower is highly dependent on the light environment of that flower.

In vegetative growth phases, the required characteristics needed for an artificial lighting source differs compared to flowering requirements. Typically, plants are much shorter in height during the vegetative phase as compared to the flowering phase, so a large degree of light penetration is not needed. Since plants are shorter, there is not a large difference in intensity from top to bottom of the plant, as not enough distance elapses from the source for significant diminishment of intensity to occur.

In some embodiments, lighting quality and spectral distribution needs also differ between the two different production areas. During vegetative growth, a smaller, squatter plant form is desirable, as finishing height of the plant in flower is highly controlled by the finished size of the vegetative plant. Shorter, more compact plants entering flowering areas from vegetative growth contribute to a more ideal plant height for flower production. A spectral distribution of the light source which includes large amounts of blue light is highly desirable for vegetative growth stage, as this will suppress internode elongation and achieve the proper growth morphology to achieve a squatter, bushier plant.

One other benefit to plasma lighting supplementation is the addition of UV-b wavelengths of light in the spectral distribution provided to the plants. Ultraviolet radiation is typically absent in 100% artificially illuminated plant production environments.

Ultraviolet radiation has been implicated in increases in potency and quality characteristics in some varieties of *Cannabis*. It has been suggested that Cannabinoids produced by the plant help protect the seeds from damage from ultraviolet radiation. By supplementing these wavelengths into plant production areas, it may influence the amount of cannabinoids and/or terpenes produced by the plant.

Carbon Dioxide Enrichment

Carbon is an essential element to plant nutrition. Carbon is taken in through the stomata during photosynthesis where it is converted into carbohydrates. *Cannabis* dry weight can be 40% elemental carbon by mass. Carbon dioxide competes with other compounds such as oxygen to activate the protein driving photosynthesis; increasing carbon dioxide levels enhances photosynthesis. In some embodiments, carbon dioxide levels are to be kept at 1500 part per million (ppm) in vegetative and flower stages of growth except the clone stage. In some embodiments, the proper level is maintained by a compressed carbon dioxide injection system, which is control by an in-flow pressure regulator and ppm monitor.

In some embodiments, to promote $CO_2$ exchange in the boundary layer between the foliage and environment, which needs to be minimized and removed, adequate air flow on both the underside, within and upper portion of the canopy, is provided. In some embodiments, fans at the benching level to promote air exchange are utilized. In some embodiments, convection tubes are utilized to provide optimal air exchange within the canopy. In some embodiments, canopy management promotes the reduction of the boundary layer, $CO_2$ exchange and proper HAF movement.

Additional Cultivation Parameters

In one embodiment, the invention relates to a method of repairing abnormal growth a plant from Cannabaceae family the wherein the lighting is increased or decreased in response to morphological changes that are expressed by the plant. These changes often include, but are not limited to: discoloration of the leaves to do malnutrition, lower or higher EC value in the growth media, and stunted vertical and/or horizontal foliage growth.

In another embodiment, the growing techniques are not limited to soil-based plant growing. This invention is widely applicable to any growing setup using a capillary mat. In one embodiment, growing techniques may include hydroponics.

In one embodiment, the invention is a change in the relative yield of specific, desired cannabinoid compound and/or change in the overall yield of cannabinoid compounds, in general, is produced by the plant by means of creating a lighting intensity gradient during the lifecycle of the plant from vegetative to flowering growth. Moreover, specific, desired cannabinoid compounds are also affected by controlling the ramp of this gradient. That is to say, the percent increase in intensity from one stage of growth to the next directly impacts the plant's ability to cope with the induced metabolic stress. In this way, the acclimation of the plant to the increased intensity is a driver toward obtaining a specific feedback from plant in terms of a desired natural plant product.

In one embodiment, the invention is a method of growing a plant of the Cannabaceae family, comprising exposing said plant to artificial light, irrigating said plant with water, and providing one or more nutrients to the plant; wherein exposing said plant to artificial light comprises one or more of: providing said artificial light at a different intensity level for at least two different non-reproductive phases of plant growth; and providing said artificial light to the plant from at least two different directions, which directions are the top, the sides, and the bottom of the plant; and optionally changing the relative positions of the plant to the artificial light by moving either or both of the plant and a source of the artificial light.

In one embodiment, the invention is a method wherein the plant is a *humulus* plant.

In one embodiment, the invention is a method of growing a *cannabis* or *humulus* plant, comprising exposing said plant to artificial light, irrigating said plant with water, and providing one or more nutrients, wherein exposing said plant to artificial light comprises: providing said artificial light at a different intensity level for plant growth phases of vegetative and flower growth; and said plants are exposed to about 125 micromoles to about 500 micromoles of light during the vegetative phase and from about 400 micromoles to about 975 micromoles of light during the flower phase of growth; and providing said artificial light to the plant from one or more different directions, which directions are the top, the sides, and the bottom of the plant; and optionally changing the relative positions of the plant to the artificial light by moving either or both of the plant and a source of the artificial light.

In one embodiment, the invention is a method wherein the intensity of lighting provided to the plant is increased by at least 3% each day for at least a portion of the life cycle of the plant. In one embodiment, the portion of the life cycle occurs during the cloning stage, the vegetative stage, and/or the flowering stage.

In one embodiment, the invention is a method wherein the light intensity is increased at least 7% on every fourth day for at least a portion of the life cycle of the plant. In one embodiment, the portion of the life cycle occurs during the cloning stage, the vegetative stage, and/or the flowering stage.

In one embodiment, the invention is a method wherein the increase is at least 3% and occurs on random days during growth; provided that there is at least one increase within a five day period.

In one embodiment, the invention is a method wherein one or more sources of artificial light is stationary and the plant is moving.

In one embodiment, the invention is a method wherein the plant is stationary and one or more sources of artificial light is moving.

In one embodiment, the invention is a method wherein at least one of: the duration of a given phase and/or the level of lighting intensity in a given phase is adjusted dependent upon at least one parameter selected from the group consisting of: humidity in the atmosphere, temperature of the atmosphere, over and/or under fertilization of one or more of the plants, ammonium toxicity of one or more of the plants, low root zone temperature of one or more of the plants, circulation of the atmosphere, crowding and/or stretching of one or more of the plants, and leaf temperature of one or more of the plants.

In one embodiment, the invention is a method of wherein the humidity in the atmosphere, temperature of the atmosphere, circulation of the atmosphere, fertilizer content of one or more of the plants, or crowding and/or stretching of one or more of the plants is adjusted dependent upon the desired duration of a given growth phase and/or the level of lighting intensity in a given growth phase.

In one embodiment, the method as described herein further comprises growing the plants using a capillary mat for irrigation and nutrient delivery. In some embodiments, the *cannabis* plants are irrigated using a capillary mat, which is capable of simultaneously irrigating the plants and delivering a selected set of nutrients for cultivation. The variation of the selected set of nutrients or concentration of the selected set of nutrients is provided under controlled and reproducible conditions by the capillary mat so as to provide plasticity to express substantially the same cannabinoid components within the *cannabis* plant. The *cannabis* plants can adaptively produce substantially the same cannabinoid components using the capillary mat system even if its environment changes or there are differences between various culturing conditions. The use of a capillary mat for nutrient delivery is described in U.S. patent application Ser. No. 14/871,926, filed Sep. 30, 2015 (claiming priority to U.S. Provisional Patent App. No. 62/057,974) and titled "METHODS OF *CANNABIS* CULTIVATION USING A CAPILLARY MAT."

In one embodiment, the invention is a composition produced from the methods of growing a plant as described herein.

In one embodiment, the invention is a composition, produced from the methods of growing a plant described herein, said composition comprising an assayable combined Δ9-tetrahydrocannabinol and tetrahydrocannabinolic acid concentration of less than about 2% by weight, less than about 1% by weight, less than about 0.7% by weight, less than about 0.1% by weight, less than about 0.05% by weight.

In one embodiment, the composition comprises a ratio of cannabidiol and/or cannabidiolic acid (or active CBD) to Δ9-tetrahydrocannabinol and/or tetrahydrocannabinolic acid (or active THC) of about 25:1 to about 300:1. In one embodiment, the ratio of active cannabidiol to active THC is between about 300:1 and about 30:1. In one embodiment, the ratio of active cannabidiol to active THC is between about 300:1 and about 50:1. In one embodiment, the ratio of active cannabidiol to active THC is between about 300:1 and about 70:1. In one embodiment, the ratio of active cannabidiol to active THC is between about 300:1 and about 80:1. In one embodiment, the ratio of active cannabidiol to active THC is between about 300:1 and about 100:1. In one embodiment, the ratio of active cannabidiol to active THC is between about 300:1 and about 200:1.

In one embodiment, the invention is a composition, produced from the methods of growing a plant described herein, said composition comprising an assayable ratio of cannabidiol and/or cannabidiolic acid to 49-tetrahydrocannabinol and/or tetrahydrocannabinolic acid between between about 300:1 and about 25:1.

In one embodiment, the invention is a *cannabis* product, *cannabis* cultivar, seed, or clone produced from the methods of growing a plant which are described herein.

EXAMPLES

Example 1: *Cannabis* Composition of Cultivar A

The *cannabis* cultivar A was grown according to the methods described herein, harvested and dried, and an inflorescence was taken as a sample for analysis.

The sample was tested for cannabinoid content. The values are shown in Table 1. Total assayable cannabinoid concentration was determined to be approximately 22.79%. Moisture content was approximately 9.23%.

TABLE 1

| Assayable Cannabinoids (% by weight) | | Active Cannabinoids (estimated; % by weight) | |
|---|---|---|---|
| CBD-A | 21.77 | Max CBD | 20.03 |
| CBD | 0.94 | | |
| THC-A | 0.08 | Max THC | 0.07 |
| THC | <0.001 | | |
| CBN | <0.001 | | |

The sample contained less than 0.001% each of CBD-V, CBG, THC-V, and CBC.

What is claimed is:

1. A method of growing a *cannabis* plant, comprising exposing said plant to artificial light, irrigating said plant with water, and providing said plant with one or more nutrients;
   wherein exposing said plant to artificial light comprises:
      exposing said plant to a vegetative light intensity level of about 125 micromoles $m^{-2}$ $s^{-1}$ to about 500 micromoles $m^{-2}$ $s^{-1}$ during vegetative growth phase, and
      exposing said plant to a flowering light intensity level from about 400 micromoles $m^{-2}$ $s^{-1}$ to about 975 micromoles $m^{-2}$ $s^{-1}$ during flower growth phase;
   wherein said plant comprises a top, sides and a bottom, wherein said artificial light is provided to the plant from one or more different directions selected from the group consisting of the plant top, the plant sides, and the plant bottom through one or more sources of artificial light, and wherein the vegetative and/or flowering light intensity level(s) provided to the plant are increased by at least 3% on random days during the vegetative and/or flowering growth phase, provided that there is at least one increase within a five day period; and optionally changing relative positions of the plant to the artificial light by moving either the plant and/or the one or more of the sources of artificial light.

2. The method of claim 1, wherein the one or more sources of artificial light are stationary and the plant can be moved.

3. The method of claim 1, wherein the plant is stationary and the one or more sources of artificial light can be moved.

4. The method of claim 1, wherein the water and nutrient(s) are provided to the plant by a capillary mat.

5. A method of growing a *cannabis* plant, comprising exposing said plant to artificial light, irrigating said plant with water, and providing said plant with one or more nutrients: wherein exposing said plant to artificial light comprises:
   exposing said plant to a vegetative light intensity level of about 125 micromoles $m^{-2}$ $s^{-1}$ to about 500 micromoles $m^{-2}$ $s^{-1}$ during vegetative growth phase, and
   exposing said plant to a flowering light intensity level from about 400 micromoles $m^{-2}$ $s^{-1}$ to about 975 micromoles $m^{-2}$ $s^{-1}$ during flower growth phase;
wherein said plant comprises a top, sides and a bottom, wherein said artificial light is provided to the plant from one or more different directions selected from the group consisting of the plant top, the plant sides, and the plant bottom through one or more sources of artificial light, and wherein the vegetative and/or flowering light intensity level(s) provided to the plant are increased by at least 3% each day for at least a portion of the vegetative growth phase and/or flower growth phase; and optionally changing relative positions of the plant to the artificial light by moving either the plant and/or the one or more of the sources of artificial light.

6. A method of growing a *cannabis* plant, comprising exposing said plant to artificial light, irrigating said plant with water, and providing said plant with one or more nutrients; wherein exposing said plant to artificial light comprises:
   exposing said plant to a vegetative light intensity light of about 125 micromoles $m^{-2}$ $s^{-1}$ to about 500 micromoles $m^{-2}$ $s^{-1}$ during vegetative growth phase, and
   exposing said plant to a flowering light intensity level from about 400 micromoles $m^{-2}$ $s^{-1}$ to about 975 micromoles $m^{-2}$ $s^{-1}$ during flower growth phase;
wherein said plant comprises a top, sides and a bottom, wherein said artificial light is provided to the plant from one or more different directions selected from the group consisting of the plant top, the plant sides, and the plant bottom through one or more sources of artificial light and wherein the vegetative and/or flowering light intensity level(s) provided to the plant are increased by at least 7% on every fourth day for at least a portion of the vegetative growth phase and/or the plant flower growth phase; and optionally changing relative positions of the plant to the artificial light by moving either the plant and/or the one or more of the sources artificial light.

7. A method of growing a *cannabis* plant, comprising exposing said plant to artificial light; wherein exposing said plant to artificial light comprises:
   providing said artificial light at different intensity levels during each of the *cannabis* plant's growth stages, said growth stages comprising Clone Stage 1, Clone Stage 2, Vegetative Stage 1, Vegetative Stage 2, Vegetative Stage 3, Newly Initiated Flowering Plant Stage, and Midflower Until Harvest Stage, wherein:
   said *cannabis* plant is exposed to about 105-165 micromoles $m^{-2}$ $s^{-1}$ during the Clone Stage 1, up to 7 days from cutting said *cannabis* plant;
   said *cannabis* plant is exposed to about 150-215 micromoles $m^{-2}$ $s^{-1}$ during the Clone Stage 2, 7-13 days from the cutting said *cannabis* plant;
   said *cannabis* plant is exposed to about 200-270 micromoles $m^{-2}$ $s^{-1}$ during the Vegetative Stage 1, through day 10-21 from transplant of said *cannabis* plant;
   said *cannabis* plant is exposed to about 260-350 micromoles $m^{-2}$ $s^{-1}$ during the Vegetative Stage 2, through day 20-31 from transplant of said *cannabis* plant;
   said *cannabis* plant is exposed to about 320-500 micromoles $m^{-2}$ $s^{-1}$ during the Vegetative Stage 3, through day 30-46 from the transplant of said *cannabis* plant;
   said *cannabis* plant is exposed to about 450-1100 micromoles $m^{-2}$ $s^{-1}$ during the Newly Initiated Flowering Plant Stage, through day 1-20 of flowering of said *cannabis* plant; and
   said *cannabis* plant is exposed to about 950-1100 micromoles $m^{-2}$ $s^{-1}$ during the Midflower Until Harvest Stage, from day 20 after the flowering, until an end of flowering.

* * * * *